US010251641B2

(12) United States Patent
Lenihan et al.

(10) Patent No.: US 10,251,641 B2
(45) Date of Patent: Apr. 9, 2019

(54) METHODS, SYSTEMS AND DEVICES FOR ATTACHING SURGICAL SUTURES TO SURGICAL NEEDLES AND TESTING ARMED SURGICAL NEEDLES

(71) Applicant: Ethicon, Inc., Somerville, NJ (US)

(72) Inventors: Timothy P. Lenihan, Morrisville, PA (US); Yasemar Perez, Aguadilla, PR (US)

(73) Assignee: Ethicon, Inc., Somerville, NJ (US)

( * ) Notice: Subject to any disclaimer, the term of this patent is extended or adjusted under 35 U.S.C. 154(b) by 123 days.

(21) Appl. No.: 15/403,502

(22) Filed: Jan. 11, 2017

(65) Prior Publication Data

US 2018/0193017 A1    Jul. 12, 2018

(51) Int. Cl.
*A61B 17/06* (2006.01)
*A61B 17/04* (2006.01)
*A61B 17/00* (2006.01)

(52) U.S. Cl.
CPC .... *A61B 17/06004* (2013.01); *A61B 17/0467* (2013.01); *A61B 17/06061* (2013.01);
(Continued)

(58) Field of Classification Search
CPC combination set(s) only.
See application file for complete search history.

(56) References Cited

U.S. PATENT DOCUMENTS 3,875,946 A    4/1975 Duncan
3,980,177 A    9/1976 McGregor
(Continued)

FOREIGN PATENT DOCUMENTS

JP    S63212028    9/1988

OTHER PUBLICATIONS

SMAC Moving Coil Actuators, SMAC Corporation of Carlsbad, California, www.smac-mca.com/technical-resources/moving-coil-technology, 2017, 2 pages.
(Continued)

*Primary Examiner* — Sarang Afzali
*Assistant Examiner* — Ruth G Hidalgo-Hernandez
(74) *Attorney, Agent, or Firm* — Doherty IP Law Group LLC

(57) ABSTRACT

A method of attaching a surgical suture to a needle and testing the attachment includes dispensing a length of suture from a spool by using a first suture gripper, and using a surgical needle gripper for holding a surgical needle stationary. A leading end of the suture is inserted into and attached to a receiving end of the surgical needle. A second suture gripper is located between the first suture gripper and the spool. After the second suture gripper is closed for gripping the suture, the second suture gripper is advanced downstream toward the surgical needle to reduce the tension on the suture. The tension on the suture is reduced by moving the second suture gripper a pre-determined distance. The first suture gripper is opened for releasing the suture and the first suture gripper is moved toward the suture spool for re-grasping the suture at a location between the second gripper and the suture spool. The suture between the downstream side of the re-positioned first suture gripper and upstream side of the second suture gripper is cut. After the suture is cut, the second suture gripper is displaced toward the spool using a tension control system to increase the tension level between the needle and the second suture gripper.

9 Claims, 6 Drawing Sheets

(52) U.S. Cl.
CPC .............. *A61B 2017/00526* (2013.01); *A61B 2017/06028* (2013.01); *Y10T 29/49929* (2015.01)

(56) References Cited

U.S. PATENT DOCUMENTS

| | | |
|---|---|---|
| 4,799,311 A | 1/1989 | Matsutani |
| 4,922,904 A | 5/1990 | Utake et al. |
| 5,487,308 A | 1/1996 | Demarest et al. |
| 5,873,212 A | 2/1999 | Esteves et al. |
| 5,918,284 A | 6/1999 | Blanch et al. |
| 5,937,504 A | 8/1999 | Esteves et al. |
| 6,076,255 A | 6/2000 | Shikakubo et al. |
| 6,081,981 A | 7/2000 | Demarest et al. |
| 6,647,803 B1 | 11/2003 | Demarest et al. |
| 6,800,231 B2 | 10/2004 | Demarest et al. |
| 7,185,411 B2 | 3/2007 | Lenihan et al. |
| 8,214,996 B2 | 7/2012 | Stametz et al. |
| 8,402,623 B2 | 3/2013 | Price et al. |

OTHER PUBLICATIONS

International Search Report issued by the International Searching Authority in corresponding International Application No. PCT/IB2018/050086, dated Mar. 15, 2018, 3 pages.
Written Opinion of the International Searching Authority in corresponding International Application No. PCT/IB2018/050086, dated Mar. 15, 2018, 6 pages.
English language translation of JP S63 212028, 5 pages.

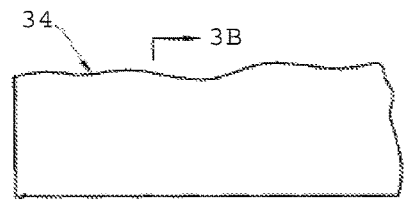
FIG. 3A
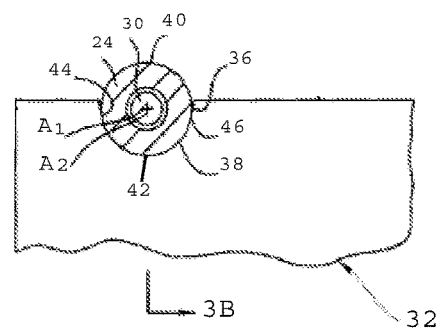
FIG. 3B
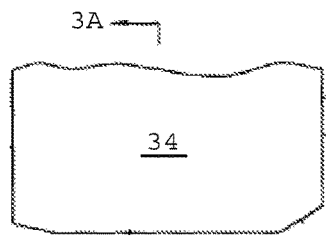
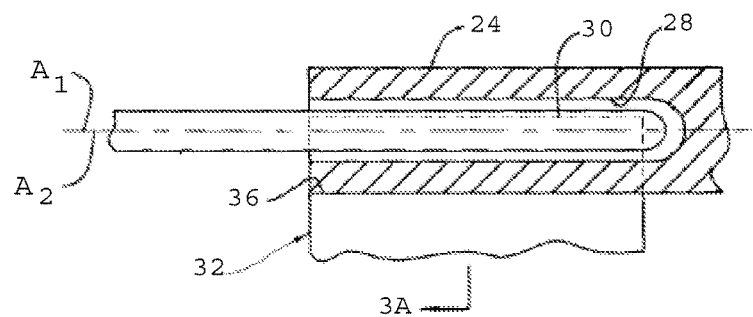

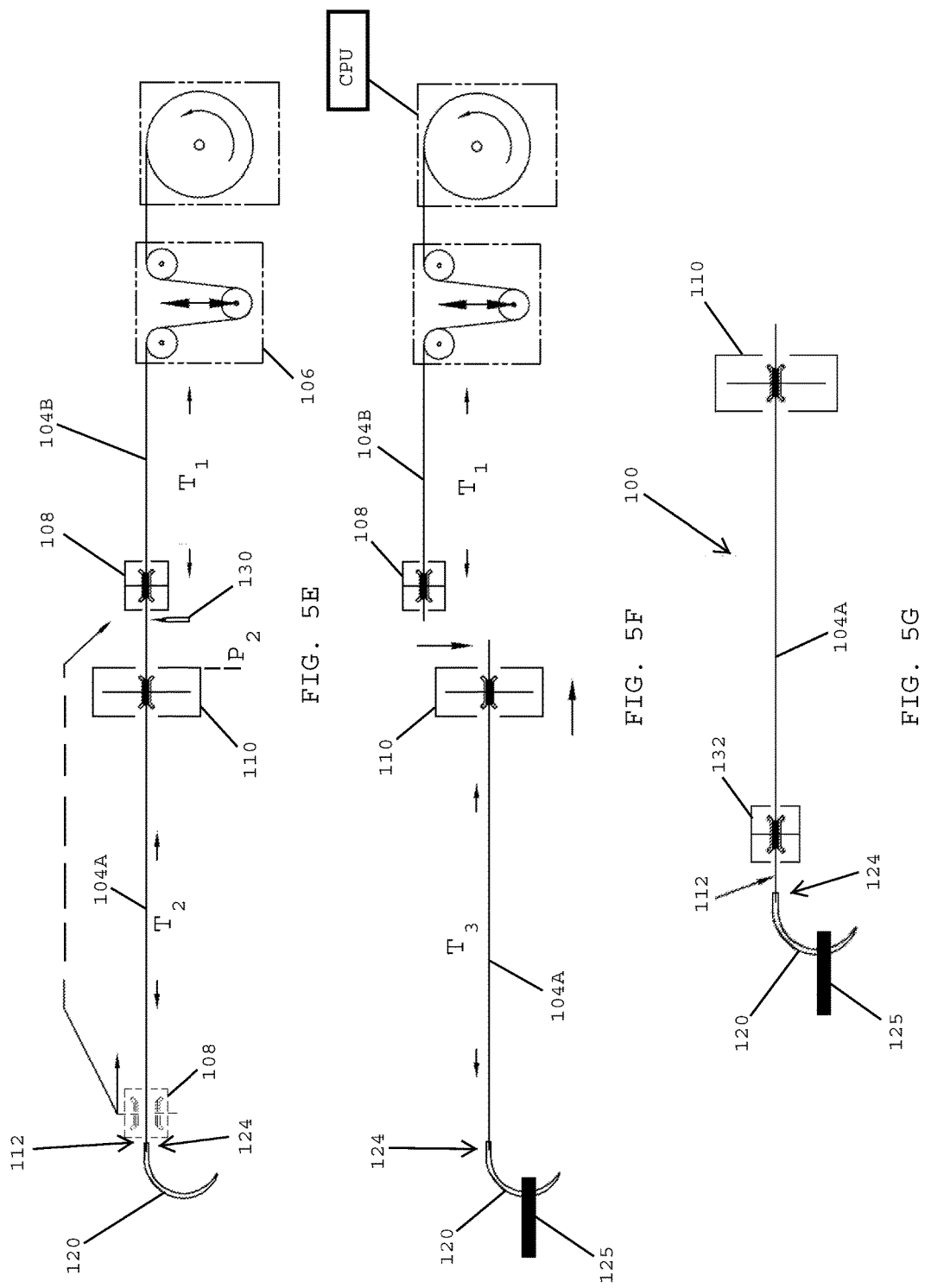

METHODS, SYSTEMS AND DEVICES FOR ATTACHING SURGICAL SUTURES TO SURGICAL NEEDLES AND TESTING ARMED SURGICAL NEEDLES

BACKGROUND OF THE INVENTION

Field of the Invention

The present patent application is generally directed to armed surgical needles having a suture attached to an end of a surgical needle, and is more particularly directed to automated swage machines for making armed surgical needles.

Description of the Related Art

Armed surgical needles, i.e., needles having sutures attached to one end thereof, are typically manufactured utilizing manual, semi-automated, and fully automated procedures that feed a length of suture material into a suture receiving opening of a surgical needle, and that swage (i.e., compress) the surgical needle to the suture tip.

Swaging needles to sutures typically involves inserting the free end of a suture into an axial bore of a needle barrel of a surgical needle, and holding the suture inside the axial bore while a swage die impinges upon the outer surface of the needle barrel, thereby compressing a portion of the bore onto the suture. The compressed portion of the axial bore grasps the suture by mechanical interference and by surface friction. The swaging process is conducted to create an attachment between the needle barrel and the suture that meets or exceeds "pull-out" strength standards.

One approach to providing good suture attachment is multiple hit swaging, wherein a needle is subjected to swaging of a controlled depth, however, the compression is distributed over a large area of the needle barrel (e.g., around the circumference of the needle barrel). To achieve this type of swaging, the needle may be rotated relative to the swaging dies between multiple swaging compressions. In this manner, multiple angularly offset swaging operations are performed to attach a single needle to a single suture. While this approach provides a reliable attachment, each hit on the barrel of the needle produces stress in the needle barrel and the suture. The needle and suture materials have some degree of malleability, but when the limit of malleability is reached, the materials will fail, leading to, in the case of the needle, cracking and loss of attachment, or breakage. Cracking is a particular problem when harder alloys are used, including advanced alloys such as 4310 SS, nickel-titanium SS, and 420 SS. Further, needle materials have some elasticity, such that the relief of residual stress causes the needle barrel to relax over time, leading to a loss of attachment between the needle bore and the suture.

One advance directed to minimize failure of the parts during a swaging operation is disclosed in commonly assigned U.S. Pat. No. 8,214,996 to Stametz et al., the disclosure of which is hereby incorporated by reference herein. In one embodiment, the '996 patent discloses a method of attaching a suture to a needle barrel. In one embodiment, a first compression stroke compresses a radial top of a needle barrel against a suture that has been inserted into a bore of the needle barrel while restraining the radial bottom and radial sides of the needle barrel against deformation. A second compression stroke compresses the bottom of the barrel against the suture while restraining the sides against deformation. In another embodiment, the top and bottom sides of a needle barrel are compressed while the opposing lateral sides of the needle barrel are restrained against deformation. In one embodiment, an apparatus for attaching a suture to a needle barrel includes two die sets, each including a die with a groove therein. In one die set, the groove protects the bottom and lateral sides of the needle barrel from deformation while the top is compressed. In the other die set, the groove protects the lateral sides of the needle barrel from deformation while the bottom of the needle barrel is compressed.

There have been many efforts directed to automatically forming armed needles. For example, commonly assigned U.S. Pat. No. 6,081,981 to Demarest et al., the disclosure of which is hereby incorporated by reference herein, teaches a method for automatically forming armed surgical needles and for automatically packaging the armed surgical needles in a packaging tray. In one embodiment, the method includes sorting and depositing a plurality of needles on an indexing conveyor; enabling a robot gripper device to sequentially pick up the needles and place a picked needle in a precision conveyor device for automatic sequential conveyance to a first station; utilizing a first indexing device for sequentially indexing the needle from the first station to a second station to form the armed needle, the first indexing device being elevated in height; at the second station, automatically inserting a free end of a suture strand into the suture receiving opening of the needle, swaging the needle about the free end of the suture, and cutting the suture strand to a predetermined definite length to form the armed needle. In one embodiment, the formed armed needle is sequentially inserted into a respective single package tray indexed at a subsequent station that has been oriented in height with respect to the first indexing device in accordance with the size of the needle. At a further subsequent station, the tray and parked armed needle therein is subject to at least one rapid winding operation to wind the suture around a peripheral channel of the tray.

Commonly assigned U.S. Pat. No. 7,185,411 to Lenihan et al., the disclosure of which is hereby incorporated by reference herein, teaches an apparatus for forming armed sutures including a swaging station for receiving, holding and swaging needles that are deposited therein. In one embodiment, a linear motor drives a suture insertion gripper, which pulls suture from a supply reel and inserts a cut end on the suture into a needle held in the swaging station. A ganged needle transfer assembly with a plurality of spaced needle gripper units carries needles along a line substantially at right angles to the suture line and transfers the needles to and from the swaging station and other needle processing stations. In one embodiment, a precisor orients needles prior to placement in the swaging station and a pull test assembly tests armed sutures in both destructive and non-destructive modes. Both ends of the production line may be automated, e.g., by robots which load and offload needles prior to and after swaging, respectively. The apparatus is capable of forming double armed sutures by using a rotatable mount for the suture insertion gripper and a secondary, loop gripper. A suture transfer gripper extends up to the suture from a multi-tiered stack of slide tables. The suture transfer gripper cooperates with the suture insertion and loop grippers to hold the suture during cutting, insertion and transfer to the pull test apparatus and thereby protects the suture during processing.

After armed needles are formed, they must be tested to determine if they satisfy certain requirements demanded by surgeons. For example, U.S. Pat. No. 3,980,177 discloses a requirement of a surgeon or medical personnel to be able to detach an armed surgical needle from a suture after suturing to avoid the necessity of cutting the suture with scissors. The '177 patent discloses a needle-suture combination having a straight pull-out value of between about three (3) ounces and 26 ounces depending upon the size of the suture. The '177 patent, however, does not disclose a means for testing the armed surgical needle to determine its pull-out value, i.e., the force necessary to detach the needle from the suture.

U.S. Pat. No. 4,922,904 discloses a system for confirming whether a length of suture has been firmly connected to a surgical needle or not by applying tension to the suture after a swaging step and prior to cutting the suture. The '904 patent does not disclose a method for determining the amount of force that is required to separate the needle from the suture.

Commonly assigned U.S. Pat. No. 5,487,308 to Demarest et al., the disclosure of which is hereby incorporated by reference herein, teaches an automatic pull-testing apparatus for testing the strength of an armed surgical needle. In one embodiment, the apparatus includes a supporting blade for supporting a suture receiving end of an armed needle and having at least one suture receiving guide therein. A first gripping device is provided for releasably retaining the armed needle in an oriented position, and for positioning the armed needle at the supporting blade to enable the suture strand depending therefrom to be threaded at a suture receiving guide. A second suture gripper grips the suture at a position below the suture receiving guide of the supporting blade. A slide block counterweighted to a predetermined weight is connected to the second suture gripper for applying a controlled positive downward force upon the suture strand. When the first gripping device releases its grip upon the armed needle and the second gripping device and the slide block is released, a positive downward force is applied to the suture strand to perform a minimum pull-test of the armed needle. A destructive pull test is also performed by a device that generates a positive force against the slide block that is sufficient to dislodge the suture from the needle.

In spite of the above advances, there remains a need for Flexible Automatic Swage (FAS) machines that efficiently and effectively produce armed surgical needles to exacting standards including high reliability and low failure rates. In spite of the above advances, there is a continuing need for.

SUMMARY OF THE INVENTION

In one embodiment, an automated method of attaching a surgical suture to a surgical needle preferably includes providing a surgical suture having a leading end and a trailing end, using a first suture gripper to secure the leading end of the surgical suture, advancing the first suture gripper downstream toward a surgical needle having a suture receiving end and inserting the leading end of the surgical suture into the suture receiving end of the surgical needle, whereby the first suture gripper applies a first tension level to the surgical suture.

In one embodiment, the method preferably includes performing a swaging operation for attaching the leading end of the surgical suture to the suture receiving end of the surgical needle while maintaining the first tension level on the surgical suture, using a second suture gripper to secure the surgical suture at a location that is upstream from the first suture gripper, and advancing the second suture gripper downstream toward the first suture gripper and the surgical needle for reducing the tension applied to a section of the surgical suture that extends between the second suture gripper and the surgical needle to a second tension level that is less than the first tension level.

In one embodiment, after the reducing the tension step, the first suture gripper is released from the leading end of the surgical suture and the first suture gripper is moved to a location that is upstream from the second suture gripper. After the releasing and moving the first suture gripper steps, the method desirably includes closing the first suture gripper to secure a section of the surgical suture at a location upstream of the second suture gripper, and cutting the surgical suture at a location between the first and second suture grippers to form a cut suture section that extends between the surgical needle and the second suture gripper.

In one embodiment, during the cutting the suture step, the tension applied to the suture between the first suture gripper and the second suture gripper is about 50-200 grams, and the tension applied to the suture between the second suture gripper and the surgical needle is about 15-25 grams.

In one embodiment, the method includes securing the surgical needle using a needle gripper, and after the cutting step, using the needle gripper and the second suture gripper to transfer the surgical needle and the cut suture section to a pull test station. In one embodiment, the method desirably includes moving the second suture gripper away from the needle gripper as the surgical needle and the cut suture section are transferred to the pull test station for increasing the tension in the cut suture section from the second tension level to a third tension level that is greater than the second tension level. In one embodiment, the first tension level is about 50-200 grams, the second tension level is about 15-25 grams, and the third tension level is about 40 grams.

In one embodiment, the method preferably includes at the pull test station, using a third suture gripper to secure the cut suture section at a location between the surgical needle and the second suture gripper, and moving the third suture gripper away from the surgical needle for increasing tension on the cut suture section to a fourth tension level that is greater than the third tension level.

In one embodiment, the automated system includes a suture spool having suture material wound onto the spool. In one embodiment, the method preferably includes using the first suture gripper for dispensing a length of the surgical suture from the spool of suture, and passing the dispensed length of the surgical suture though a tension device located between the spool of suture and the first suture gripper for maintaining tension applied to the dispensed length of surgical suture at the first tension level In one embodiment, the first and third suture grippers include electric cylinders, and the second suture gripper device is a programmable electric actuator including moving coil technology or voice coil actuator technology.

In one embodiment, a system preferably includes a central processing unit for automatically controlling operation of the first, second and third suture grippers and the needle gripper. In one embodiment, the central processing unit contains different programs for manufacturing armed surgical needles having differently sized surgical needles and differently sized sutures.

In one embodiment, a method of attaching a surgical suture to a surgical needle preferably includes providing a spool having surgical suture wound about the spool, passing a leading end of the surgical suture through a tension device, providing a first suture gripper located at an initial position and closing the first suture gripper to secure the leading end of the surgical suture, and advancing the first suture gripper downstream toward a surgical needle having a suture receiving end and inserting the leading end of the surgical suture into the suture receiving end of the surgical needle, wherein the first suture gripper applies a first tension level to a section of the surgical suture that extends between the first suture gripper and the tension device.

In one embodiment, the method desirably includes attaching the leading end of the surgical suture to the suture receiving end of the surgical needle while maintaining the first tension level on the surgical suture, using a second suture gripper to secure the surgical suture at a location that is upstream from the first suture gripper, advancing the second suture gripper downstream toward the surgical needle for reducing the tension applied to a section of the surgical suture that extends between the second suture gripper and the surgical needle to a second tension level that is less than the first tension level, and after the reducing the tension step, releasing the first suture gripper from the leading end of the surgical suture and moving the first suture gripper upstream to the initial position. In one embodiment, after the releasing and moving the first suture gripper steps, the first suture gripper is preferably closed to secure a section of the surgical suture extending between the second suture gripper and the tension device, and the surgical suture is cut at a location between the first and second suture grippers to form a cut suture section that extends between the surgical needle and the second suture gripper.

In one embodiment, a method preferably includes securing the surgical needle using a needle gripper, and after the cutting step, using the needle gripper and the second suture gripper to transfer the surgical needle and the cut suture section to a pull test station. In one embodiment, the second suture gripper is moved away from the surgical needle as the surgical needle and the cut suture section are transferred to the pull test station for increasing the tension in the cut suture section from the second tension level to a third tension level that is greater than the second tension level and less than the first tension level.

In one embodiment, the method includes at the pull test station, using a third suture gripper to secure the cut suture section extending between the surgical needle and the second suture gripper, and moving the third suture gripper away from the surgical needle for increasing tension in the cut suture section to a fourth tension level that is greater than the third tension level.

In one embodiment, the first tension level is between about 50-250 grams, the second tension level is between about 10-20 grams, and the third tension level is between about 20-40 grams. In one embodiment, the first tension level is about 200 grams, and the second tension level is about 20 grams.

In one embodiment, an automated system preferably includes a central processing unit for automatically controlling operation of the first, second and third suture grippers and the needle gripper, whereby the central processing unit contains different programs for manufacturing armed surgical needles using differently sized surgical needles and differently sized sutures.

In one embodiment, during the cutting step, the tension applied to the suture between the first suture gripper and the second suture gripper is about 50-200 grams, the tension applied to the suture between the second suture gripper and the surgical needle is about 15-25 grams, and the tension applied to the suture between the first suture gripper and the tension device is about 50-200 grams.

In one embodiment, a method of attaching a surgical suture to a needle and testing the attachment preferably includes dispensing a length of surgical suture from a spool of suture using a first suture gripper, and using a surgical needle gripper for holding a surgical needle stationary, the surgical needle having a suture receiving end. In one embodiment, a free, leading end of the suture is inserted into and attached to the receiving end of the surgical suture needle. In one embodiment, a second suture gripper is located between the first suture gripper and the surgical needle. In one embodiment, after the second suture gripper has closed for gripping the suture, the second suture gripper is advanced downstream toward the surgical needle to reduce the tension level on the suture. The tension on the suture may be reduced by moving the second suture gripper a pre-determined distance to reduce the tension or by changing the tension level to a pre-determined differential tension as measured by a force sensor on the second suture gripper.

In one embodiment, the first suture gripper is opened for releasing the suture and the first suture gripper is moved toward the suture spool for re-grasping the suture at a location between the second gripper and the suture spool. The suture between the downstream side of the re-positioned first suture gripper and upstream side of the second suture gripper may be cut. After the suture material is cut, the second gripping device is preferably displaced downstream toward the surgical needle using a tension control system to decrease the tension level between the needle attachment and the second gripper. In one embodiment, the suture and the surgical needle are preferably moved to a pull test station where the suture is grasped by a third suture gripper positioned between the second suture gripper and the needle. The third suture gripper is preferably utilized to increase the tension on the suture to either a pre-determined tension that is representative of a minimum acceptable attachment strength or to a tension required to separate the suture from the needle.

In one embodiment, an automated system for making armed needles includes pulling suture from a spool, inserting the suture into a hole in the end of a surgical needle, swaging (i.e., crimping) the needle or otherwise attaching the needle to the suture, cutting the suture to a required length, and transporting the needle and the suture to the next assembly for further processing.

In one embodiment, the automated system is capable of producing armed surgical needles whereby the size range of the needles is between about 12-50 mil in diameter, and the size range of the suture material is from USP 6-0 to USP 1.

When using FAS machines to manufacture armed needle, delicate suture types can be easily damaged by incidental contact between the suture and the internal components of the FAS machine. In one embodiment, in order to minimize damage to the suture, the suture is held between two grippers, which are simultaneously moved together to transfer the needle and the suture from a swaging station to a pull test station. With the suture suspended and controlled by the two grippers, the suture cannot become entangled or abraded during transfer between the two stations.

In one embodiment, in order to preserve the transport capabilities and the pull test capabilities of the armed suture, the suture is preferably transferred as described above between two grippers, and the tension applied to the suture is varied during the transfer process.

In one embodiment, the level of tension that is applied to the suture for clean cutting is above the lower limit of the Controlled Release In-Process Quality Assurance (IPQA). If the tension is not lowered below the IPQA lower limit, the attachment of the suture and needle will be exposed to a level of tension or force that could detach the suture from the needle.

In one embodiment, the second suture gripper is an actuator that incorporates a voice servo coil cylinder such as that sold by SMAC Corp. of Carlsbad, Calif. The second suture gripper preferably holds the cut trailing end of the suture. Immediately after the suture is cut and prior to opening the first suture gripper for releasing the leading end of the suture inserted into the needle opening, the second suture gripper is moved towards the needle by the SMAC unit creating a near zero suture tension. The first suture gripper is then opened with the suture tension below the IPQA lower limit. After the suture has been cut, the second suture gripper is displaced downstream toward the needle so that it is offset from its cut position. The downstream, offset position is derived at the start of each new batch by means of an automatic calibration setup procedure.

During transfer of the attached needle and suture to the pull test station, the second suture gripper raises the tension applied to the suture from "near zero" (e.g., 10-25 grams) to a target tension value (e.g., 40 grams or +25/−15 below IPQA. The purpose of increasing the tension in the suture during transfer to the pull test station is to assure that the suture is presented to the pull test station in a straight line at the lowest reasonable tension amount. Starting the minimum pull testing at a low tension reduces variability in the test results by allowing sufficient time for the pull test servo motor to stop applying additional tension.

In one embodiment, suture tension may be automatically raised and lowered by the control system of the Flexible Automatic Swage machine when securing a suture to a needle (e.g., at an automated swaging station) and at a pull test station. In one embodiment, the FAS system controller may automatically lower the suture tension below IPQA between the first suture gripper and the second suture gripper, while the suture presented to the suture cutter station remains above the IPQA lower limits, thereby allowing for a clean cut of the suture.

In one embodiment, the needle and the suture attachment are not exposed to tension above the IPQA lower limit prior to transferring the needle and attached suture to the pull test station. In one embodiment, the suture tension is raised from "near zero" tension to a consistent value for all suture types and gauges during the transfer of the needle and suture from the swaging station to the pull test station.

Providing consistent tension at the start of a Minimum Pull Test at a pull test station reduces variability in the Minimum Pull Test results, which allows the Pull Test Station's Minimum Pull Tension Set Point to be lowered (closer to the IPQA lower limit), thereby resulting in fewer sutures and needles failing due to separation. This will result in higher output yields.

These and other preferred embodiments of the present invention will be described in more detail below.

BRIEF DESCRIPTION OF THE DRAWING

FIG. 3A is a front cross-sectional view of an apparatus including a die set for attaching a surgical suture to a surgical needle.

FIG. 3B is a side cross-sectional view of the apparatus shown in FIG. 3A.

FIGS. 5A-5G show a method for attaching a surgical suture to a surgical needle and testing the attachment between the surgical suture and the surgical needle, in accordance with one embodiment of the present invention.

DETAILED DESCRIPTION OF PREFERRED EMBODIMENTS

Figure 1:
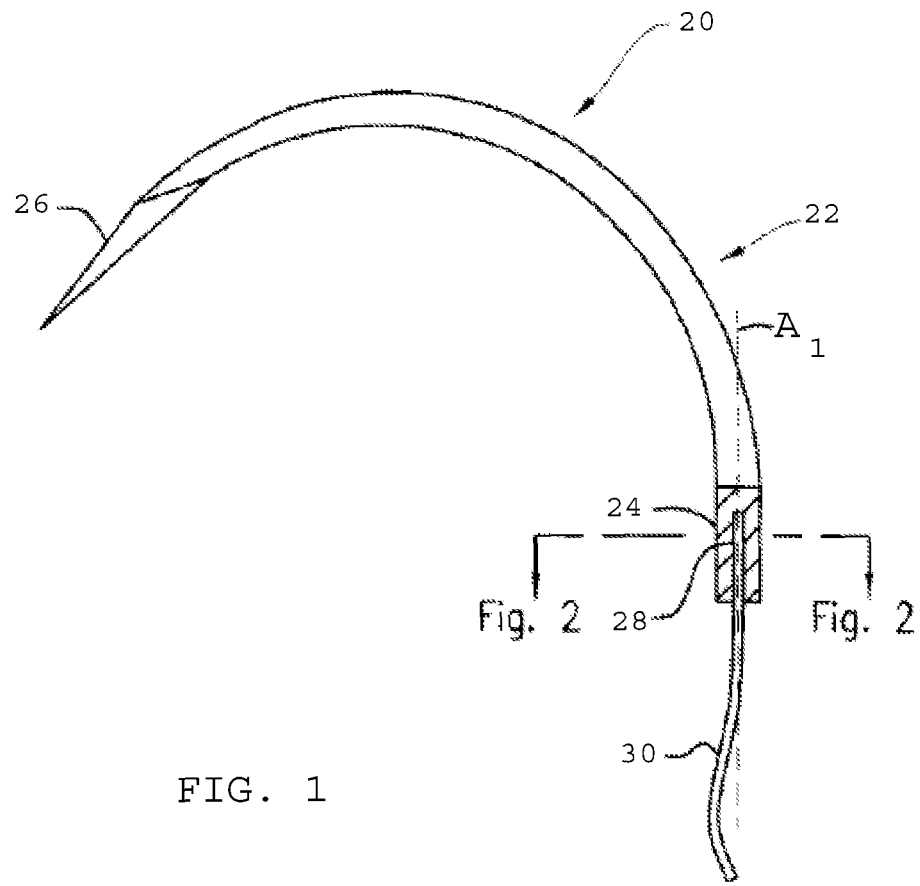
FIG. 1 shows a surgical needle and a suture secured within a needle barrel of the surgical needle, in accordance with one embodiment of the present patent application.
Figure 2:
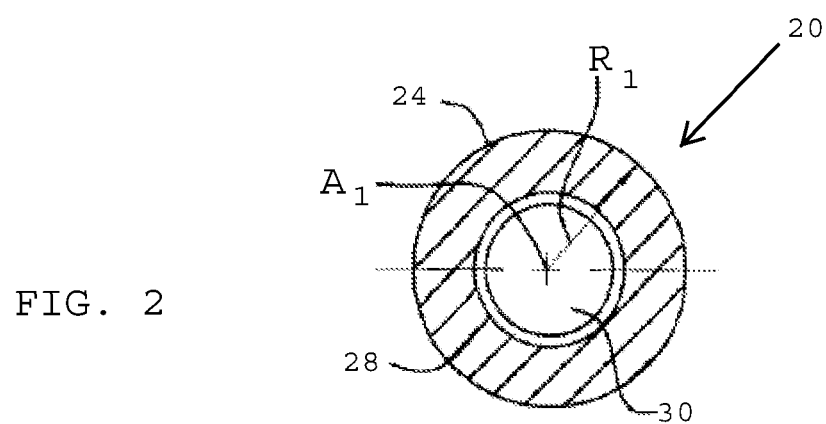
FIG. 2 is a cross-sectional view of the needle barrel and the suture shown in FIG. 1.

Referring to FIGS. 1 and 2, in one embodiment, a surgical needle 20 has a curved body 22 with a proximal end having a needle barrel 24 and a distal end having a sharpened, leading end 26. In one embodiment, the needle barrel 24 has a bore 28, such as an axial bore, that is adapted to receive a leading end of a surgical suture 30 for attaching the surgical suture to the needle barrel 24. FIG. 1 shows a cut-away view of the needle barrel 24 at the proximal end of the curved body 22 with the leading end of the surgical suture 30 inserted into the bore 28 of the needle barrel 24. In one embodiment, the bore 28 in the needle barrel 24 has an inner diameter that is equal to or larger than the outer diameter of the surgical suture 30 so that the leading end of the surgical suture may be advanced into the bore prior to a swaging step.

Referring to FIG. 2, in one embodiment, the needle barrel 24 desirably has a circular cross-section having a radius designated $R_1$ and a central longitudinal axis designated $A_1$. In one embodiment, the radius $R_1$ of the needle barrel 24 is about 0.003 inches to about 0.035 inches, and more preferably about 0.006 inches to about 0.025 inches. The surgical needle 20 may be made from a broad variety of rugged, biocompatible materials including metal alloys such as stainless steel, 4310 SS, nickel-titanium (NiTi) SS and 420 SS, or advanced alloys, such as, tungsten-rhenium (W—Re) alloys and refractory alloys. The bore 28 is desirably sized and shaped to receive the leading end of the surgical suture 30, which may be one of any number of conventional sutures or suture types that have yet to be developed. In one embodiment, the suture 30 may have a size range of USP 6-0 to USP 1.

In one embodiment, an automated system is capable of producing armed needles having a surgical needle size range of about 12-50 mil in diameter, and a suture size range of between USP 6-0 to USP 1.

FIGS. 3A and 3B show respective front and side cross-sectional views of a swaging apparatus disclosed in commonly assigned U.S. Pat. No. 8,214,996 to Stametz et al., the disclosure of which is hereby incorporated by reference herein. In one embodiment, the swaging apparatus has opposing lower and upper dies 32, 34 that close toward one another for compressing a needle barrel of a surgical needle to secure the needle barrel to a leading end of a surgical suture. In one embodiment, the lower die 32 has a groove with a curved surface 36 for receiving a needle barrel 24 of a surgical needle, and the upper die 34 positioned above the needle barrel 24. The needle barrel 24 has a first radial top portion 40 at a 12 o'clock position and second radial bottom portion 42 at a 6 o'clock position and opposing first and second lateral portions 44, 46 at the 3 o'clock and 9 o'clock positions, respectively. In one embodiment, the central longitudinal axis $A_1$ of the needle barrel 24 substantially coincides with the axis $A_2$ of the curved surface 36 formed in the lower die 32. The suture 30 is positioned within the bore 28 of the needle barrel 24.

Figure 4A:
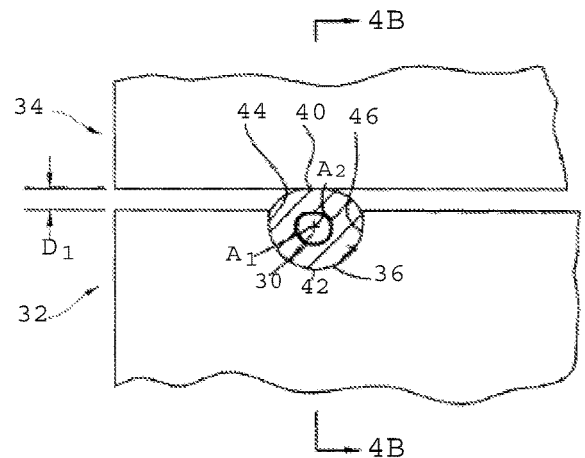
FIG. 4A is a front cross-sectional view of the apparatus of FIG. 3A during a compression stroke of a swage process.
Figure 4B:
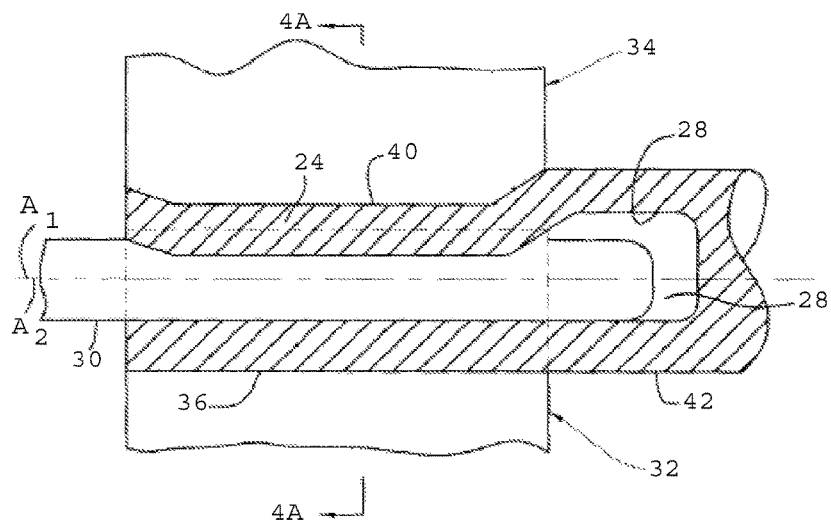
FIG. 4B is a side cross-sectional view of the apparatus of FIG. 4A.

FIGS. 4A and 4B show front and side cross-sectional views, respectively, of the lower and upper dies 32, 34, the needle barrel 24, and the surgical suture 30 during a first compression stroke of the swaging apparatus. In one embodiment, the upper die 34 moves downward toward the lower die 32 to press against, and to thereby flatten, the first radial top portion 40 of the needle barrel 24, compressing the inner surface of the bore 28 against the suture 30. The sides 44, 46 of the needle barrel 24 are restrained from becoming substantially deformed by the curved surface 36 of the groove formed in the lower die 32, which prevents the needle barrel 24 from expanding in a lateral direction (i.e., in a direction substantially perpendicular to the direction of the movement of the upper die 34). Further, the bottom outer surface 42 of the needle barrel is restrained by the curved surface 36 of the lower die 32 so that the bottom outer surface 42 is not substantially deformed. During the first compression stroke, the lower surface of the upper die 34 approaches the upper surface of the lower die 32, however, the opposing die surfaces do not contact one another. The distance $D_1$ by which the lower surface is separated from the upper surface at the end of the downward stroke of the upper die 34 may be controlled by an operator of the swaging apparatus, and may be influenced, in part, by the desired suture pull-out strength and the dimensional tolerances of the dies and the needle barrel 24. In one embodiment, compression of the top of the needle barrel 24 also shapes the needle barrel to conform to the lower surface of the upper die 34 to reduce the likelihood of weakening the needle barrel 24 or the suture 30.

Figure 5A:
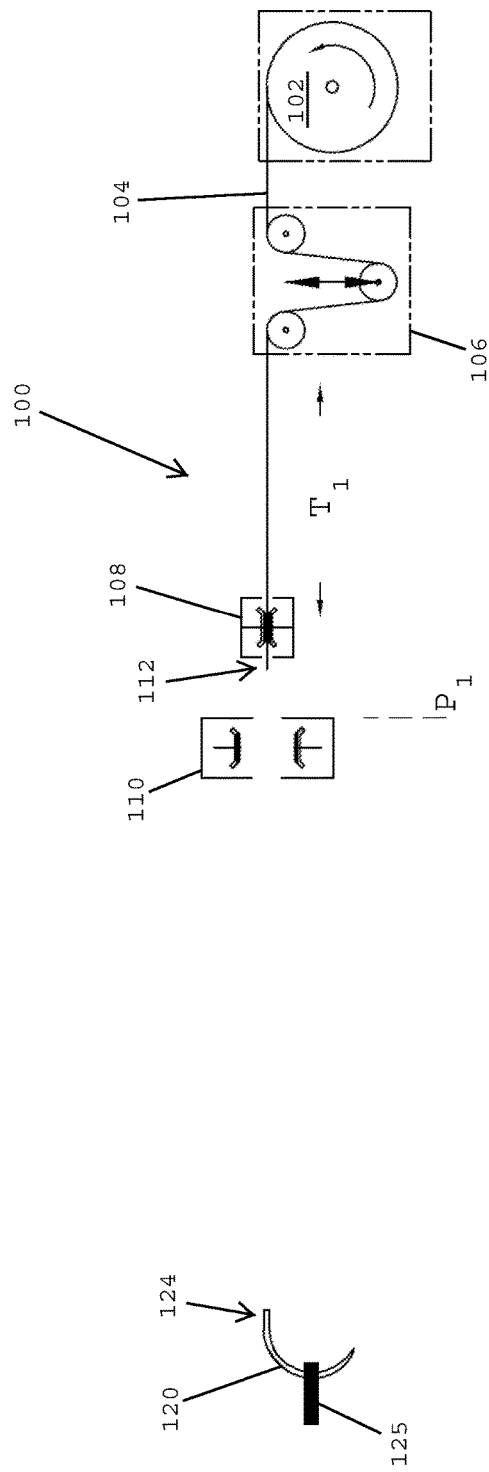

Referring to FIG. 5A, in one embodiment, an automated suture/surgical needle attaching and testing system 100 preferably includes a spool 102 having surgical suture material 104 wound about the spool 102. The automated system 100 desirably includes a tension device 106 for maintaining tension on the suture 104 as it is unwound from the suture spool 102 for attachment to a surgical needle. In one embodiment, the tension device may have rollers for guiding the suture material through the tension device. In one embodiment, a leading, free end of the surgical suture material 104 is passed through the tension device 106.

In one embodiment the suture material may be made of conventional, biocompatible, absorbable materials, non-absorbable materials, and combinations of absorbable and non-absorbable materials. Preferred non-absorbable materials include polypropylene, a polymer blend of polyvinylidene fluoride and polyvinylidene fluoride-co-hexafluoropropylene, polyethylene, polyvinylidene fluoride (PVDF), polyesters, polyethylene terephthalate, glycol-modified polyethylene terephthalate, polytetrafluoroethylene, fluoropolymers, nylons etc. and the like, or copolymers of combinations thereof. Preferred absorbable polymeric materials include polydioxanone, polyglactin, polyglycolic acid, copolymers of glycolide and lactide, polyoxaesters, and poliglecaprone. In certain preferred embodiments, the suture material may include combinations of both absorbable and non-absorbable materials. In addition, metals or ceramics may be suitable for certain applications, such as instances where specific strength or corrosion resistance is necessary. In one preferred embodiment, the suture material preferably includes a polymer blend of polyvinylidene fluoride and polyvinylidene fluoride-co-hexafluoropropylene material. In addition, any of these materials may have conventional surface modifications that include coatings, plasma treatments, therapeutics, and the like.

In one embodiment, the suture/surgical needle attaching and testing system 100 desirably includes a first suture gripper 108 that is moveable between open and closed configurations for selectively releasing and gripping the suture material 104. In one embodiment, the first suture gripper 108 desirably includes standard electric cylinders.

In one embodiment, the suture/surgical needle attaching and testing system 100 preferably includes a second suture gripper 110 that is initially located downstream from the first suture gripper 108 (i.e., the second suture gripper 110 is further away from the suture spool 102 than the first suture gripper 108). In one embodiment, the second suture gripper 110 is moveable between open and closed configurations for selectively releasing and gripping (i.e., securing) the surgical suture 104.

In one embodiment, the second suture gripper 110 is a precision, programmable electric actuator that incorporates moving coil technology, also known as voice coil actuator technology. In one embodiment, the second suture gripper incorporating moving coil technology is similar to that sold by SMAC Corporation of Carlsbad, Calif. See www.smac-mca.com/technical-resources/moving-coil-technology.

Programmable electric actuators incorporating moving coil technology provide numerous benefits over conventional electric cylinder actuators including 1) enabling force, position, and speed to be totally programmable, 2) perform at exceptionally high speeds or very low speeds, 3) perform with sub-micron accuracy and repeatability, and 4) provide extremely accurate sensing of product location and/or dimensions.

Programmable electric actuators incorporating moving coil technology are preferred for a wide range of high cycle positioning, measuring, inspection, and pick and place applications. Manufacturers desiring to increase production time, simplify set-up, and facilitate making "on the fly" adjustments to an automated swaging system during production runs can dramatically improve performance by using programmable electric actuators incorporating moving coil technology.

In one embodiment, the voice coil sits in a strong magnetic field, and a current may be passed through the coil for generating a force in either direction. The amount of force that is generated by the moving coil device is governed by the equation:

$$F \propto NIB \text{ where:}$$

F is the force generated;
N is the number of turns in the winding (Constant);
I is the current flowing through the winding; and
B is the magnetic flux (Constant).

Therefore, by controlling current, the force output may be accurately controlled.

Programmable electric actuators incorporating moving coil technology provide an ability to switch between operations-force, position and velocity mode—at any time; provide "on the fly" adjustable movement for quick changeover; provide for constant force monitoring and control; and can be programmed to decelerate smoothly and quickly so that mechanical slamming is totally eliminated.

Programmable electric actuators incorporating moving coil technology are programmable in force, acceleration and velocity, thereby providing an ability to run various products with a quick changeover using a control system, a controller, or central processing unit (CPU). A broad variety of different motion profiles and programs may be stored and preset in a control system. In one embodiment, a programmable electric actuator incorporating moving coil technology may operate in different modes: 1) Force Mode: Force Mode is open loop, using no feedback from the encoder. The actual position of the actuator is continuously monitored but has no effect upon the output. 2) Velocity Mode: Velocity Mode allows the actuating rod to be moved with a given velocity, acceleration, force and direction. 3) Position Mode: Position Mode will allow the actuating rod to be moved to various positions along the stroke using acceleration, velocity and force. In one embodiment, it is possible to perform absolute, relative and "learned position" moves.

In one embodiment, the second suture gripper 110 is programmed with a routine that allows the gripper jaw to land on the surface of a component with a low programmed force. It gives extremely accurate sensing of product location or dimensions, which is particularly useful for handling delicate or high value components. In one embodiment, the programmed routine includes a controlled low force approach in velocity mode, while the position error is constantly monitored. Once contact is made, the position error builds up until a pre-programmed figure is reached, which results in the gripper jaw maintaining position on the surface of the component.

In one embodiment, the system 100 also desirably includes a surgical needle gripper 125 for holding a surgical needle 120 stationary so that a bore formed in a needle barrel 124 at a proximal end of the surgical needle 120 opposes the leading end of the suture material 104.

In one embodiment, the suture spool 102 is located at an upstream end of the automated system 100 and the surgical needle 120 is located at a downstream end of the automated system 100. The suture material is advanced from the upstream end toward the surgical needle at the downstream end.

In one embodiment, the suture material 104 is unwound from the spool 102 and advanced downstream through the tension device 106 so that the leading end 112 of the suture material 104 may be engaged by the first suture gripper 108. In one embodiment, the first suture gripper 108 is closed for securing the leading end of the suture material 104 and unwinding the suture from the suture spool 102. During a first stage of a method for attaching the suture 104 to the surgical needle 120, the first suture gripper 108 and the tension device 106 work cooperatively to apply tension to the section of suture material 104 extending between the first suture gripper 108 and the tension device 106. In one embodiment, the tension applied to the suture 104 by the first gripper 104 and the tension device 106 is designated first tension level $T_1$. In one embodiment, the first tension level $T_1$ is about 50-200 grams.

Figure 5B:
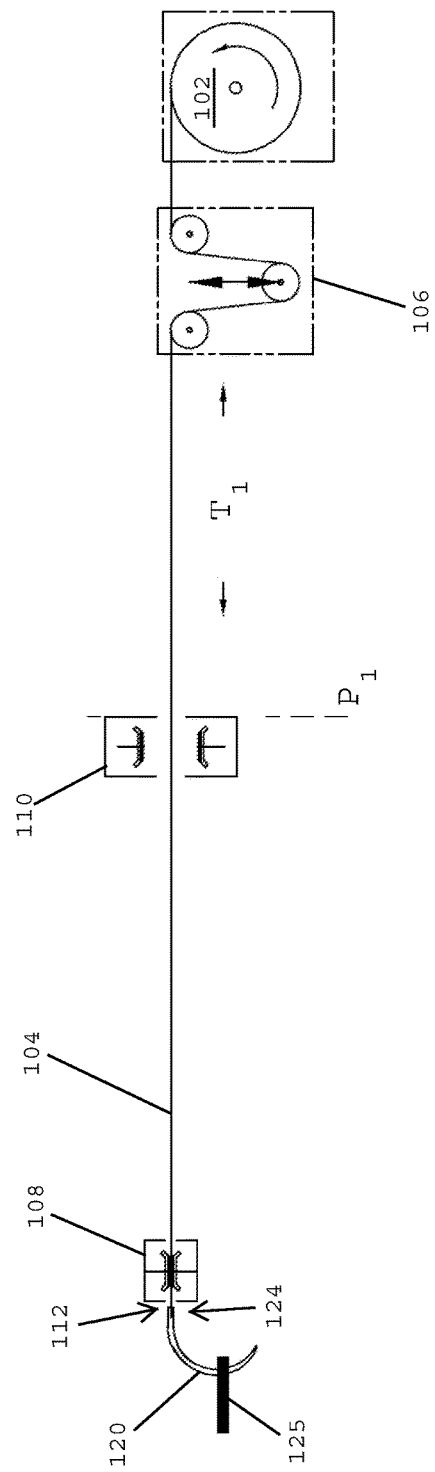

Referring to FIG. 5B, in one embodiment, the closed first suture gripper 108 grips the suture 104. During a second stage of the method for attaching the suture 104 to the surgical needle 120, the first suture gripper 108 advances downstream toward the surgical needle 120 (i.e., to the left in FIG. 5B) so that the leading end 112 of the surgical suture 104 is inserted into the bore of the needle barrel 124 of the surgical needle 120. The needle gripper 125 preferably holds the surgical needle 120 stationary as the suture is inserted into the needle barrel 124 of the surgical needle 120. The needle barrel 124 is then swaged (e.g., as described above in FIGS. 3A, 3B, 4A and 4B) for compressing the needle barrel and securing the leading end 112 of the surgical suture 104 to the needle barrel. In one embodiment, as the suture 104 is inserted into the bore of the needle barrel 124 and the needle barrel is swaged, the first suture gripper 108 and the tension device 106 maintain tension on the suture material 104 at the first tension level $T_1$ (e.g., within a range of about 50-200 grams).

In one embodiment, at the end of the second stage of the method for attaching a suture to a surgical needle, whereby the first suture gripper 108 is adjacent the surgical needle 120, the second suture gripper 110 desirably has an initial position highlighted by the vertical line designated $P_1$. In one embodiment, as the first suture gripper 108 grips the leading end 112 the suture 104 (FIG. 5B), the second suture gripper 110 is preferably located at the initial position designed $P_1$, which is upstream from the location of the first suture gripper 108. In FIG. 5B, the second suture gripper 110 is in an open configuration and is not in contact with the suture material 104.

Figure 5C:
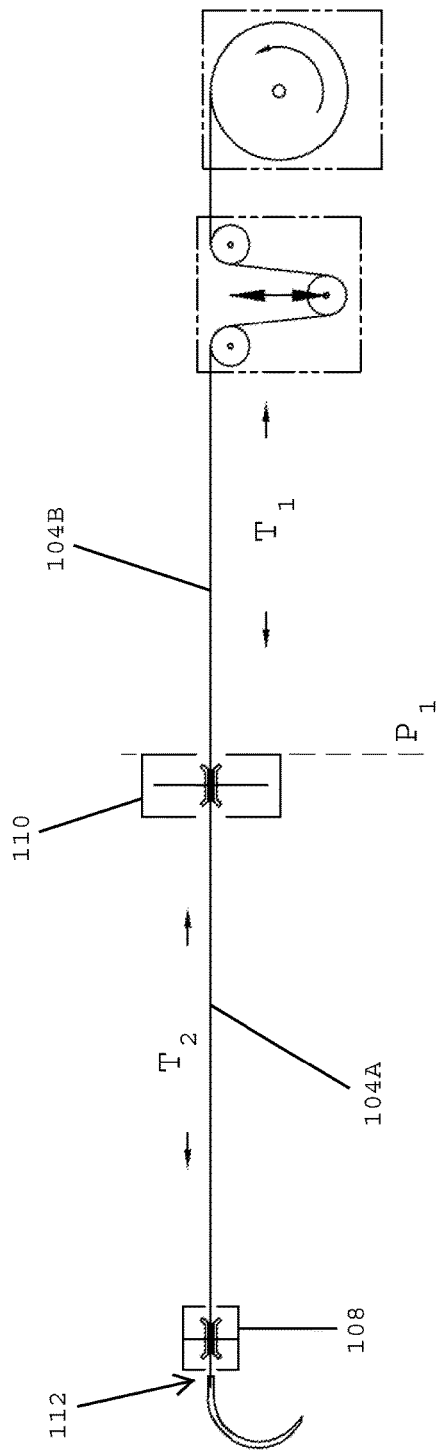

Referring to FIG. 5C, in one embodiment, during a third stage of a method for attaching a suture to a surgical needle, the first suture gripper 108 remains closed for engaging the leading end 112 of the suture 104, and the second suture gripper 110 is moved into a closed configuration for securing the suture 104 between the jaws of the second suture gripper. In the third stage, the tension level on the suture 104 is the same on both the upstream and the downstream sides of the second suture gripper 110. In one embodiment, the tension on a downstream section 104A of the suture material is at the first tension level $T_1$ (e.g., about 50-200 grams), and the tension on an upstream section 104B of the suture material is also at the first tension level $T_1$ (e.g., about 50-200 grams).

Figure 5D:
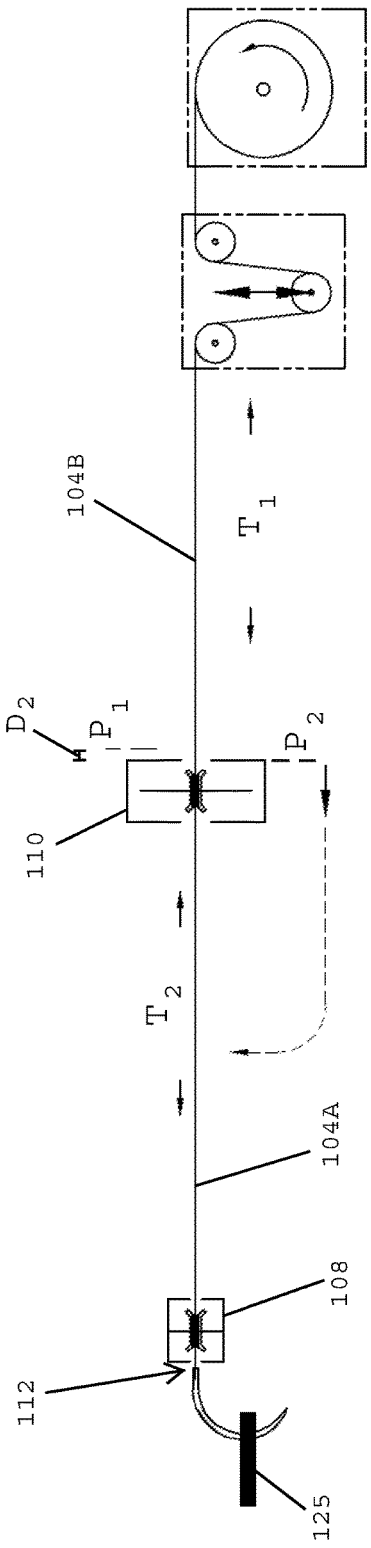

Referring to FIG. 5D, in one embodiment, during a fourth stage of a method for attaching a suture to a surgical needle, while the first suture gripper 108 remains in a closed configuration for gripping the leading end 112 of the surgical suture 104 and the needle gripper 125 hold the surgical needle 120 stationary, the closed second suture gripper 110 having voice coil technology is displaced downstream a predetermined distance $D_2$ toward the surgical needle 120. In one embodiment, the second suture gripper moves from the initial position designated $P_1$ (FIG. 5C) to a second downstream position designated $P_2$ (FIG. 5D), which is equal to the distance designated $D_2$. As a result of the downstream displacement of the second suture gripper 110, with the second suture gripper in the closed configuration for securing the suture 104, the tension on the downstream section 104A of the suture material is reduced to a second tension level $T_2$ of about 15-25 grams that is less than the tension of the upstream section 104B of the suture material, which remains at the first tension level $T_1$ of about 50-200 grams.

Referring to FIG. 5E, in one embodiment, during a fifth stage of a method for attaching a suture to a surgical needle, with the second suture gripper 110 remaining in the second displaced position designated $P_2$, the first suture gripper 108 opens to release the leading end 112 of the suture 104 that was previously attached to the needle barrel 124 of the surgical needle 120. The opened, first suture gripper 108 preferably moves back upstream to its original, start position shown in FIG. 5A above. In one embodiment, once the first suture gripper has returned to the original, start position, the first suture gripper 108 may be moved to the closed configuration for securing another section of the suture material 104 for being attached to another surgical needle. In one embodiment, the tension level between the tension device 106 and the first suture gripper 108, and between the downstream side of the first suture gripper 108 and the upstream side of the second suture gripper 110, is preferably maintained at the first tension level $T_1$ (e.g., about 50-200 grams), while the downstream section 104A of the suture between the second suture gripper and the surgical needle is at the second tension level $T_2$ (e.g., about 15-25 grams).

In one embodiment, after the first suture gripper 108 closes for securing the suture material 104, a cutting assembly 130 preferably engages a section of the suture material 104 located between the downstream side of the first suture gripper 108 and the upstream side of the second suture gripper 110 for cutting the suture 104. Immediately before the suture is cut using the cutting assembly 130, the tension on the upstream suture section 104B is at the first tension level $T_1$ (e.g., about 50-200 grams) and the tension on the downstream suture section 104A is at the second tension level $T_2$ (e.g., about 15-25 grams). The higher tension on the section of the suture to be cut makes it easier to cut the suture and ensures the formation of clean cut lines through the suture.

Referring to FIG. 5F, in one embodiment, during a sixth stage of a method for attaching a suture to a surgical needle, after the suture material has been cut to provide a cut downstream suture section 104A having a leading end secured to the needle barrel 124 of the surgical needle 120 and a trailing end secured by the second suture gripper 110, the needle gripper 125 and the second suture gripper 110 transfer the surgical needle 120 and cut suture section 104A to a pull test station. In one embodiment, as the surgical needle 120 and cut suture section 104A are carried to the pull test station, the second suture gripper 110 having voice coil technology preferably moves away from the needle barrel 124 of the surgical needle 120 for gradually increasing the tension level on the cut suture section 104A from the second tension level $T_2$ (e.g., about 15-25 grams) to a greater third tension level T3 (e.g., about 40 grams) by moving the second suture gripper 110 away from the needle barrel 124 of the surgical needle 120. The greater tension applied to the cut suture section minimizes the likelihood that the cut suture section will contact of be damaged by the components of the automated system. In one embodiment, as the surgical needle 120 and cut suture section 104A are moved to the pull test station, the first suture gripper 108 remains closed for gripping a leading end of the upstream suture section 104B. The closed first suture gripper 108 and the tension device 106 maintain the tension level of the upstream suture section 104B at the first tension level $T_1$ (e.g., about 50-200 grams).

Referring to FIG. 5F, in one embodiment, the automated system preferably includes a central processing unit (CPU) for automatically controlling operation of the first, second and third suture grippers and the needle gripper. In one embodiment, the central processing unit contains different programs for manufacturing armed surgical needles having differently sized surgical needles and differently sized sutures. A broad variety of different motion profiles and programs may be stored and preset in the CPU. In one embodiment, the CPU contains programs that enable the second suture gripper having moving coil technology to operate in different modes including: 1) A Force Mode: Force Mode is open loop, using no feedback from the encoder. The actual position of the actuator is continuously monitored but has no effect upon the output. 2) A Velocity Mode: Velocity Mode allows the actuating rod to be moved with a given velocity, acceleration, force and direction. 3) A Position Mode: Position Mode will allow the actuating rod to be moved to various positions along the stroke using acceleration, velocity and force. In one embodiment, it is possible to perform absolute, relative and "learned position" moves.

Referring to FIG. 5G, in one embodiment, the automated suture/surgical needle attaching and testing system 100 preferably includes a third suture gripper 132 that is configured to move between open and closed configurations for selectively releasing and gripping the suture material. In one embodiment, the third suture gripper 132 includes electric cylinder technology. In one embodiment, with the needle gripper 125 holding the surgical needle stationary and the second suture gripper 110 securing the tail end of the cut suture section 104A, the third suture gripper 132 is closed for gripping the cut suture section 104A adjacent the needle barrel 124 of the surgical needle 120. In one embodiment, before the third suture gripper 132 closes for securing the cut suture section 104A, the second suture gripper 110 maintains the tension level on the cut suture section 104A at the third tension level $T_3$ (e.g., about 40 grams). The third suture gripper 132 is preferably utilized for conducting a pull test on the strength of the attachment between the needle barrel 124 and the leading end of the cut suture section 104A secured within the needle barrel.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A method of attaching a surgical suture to a surgical needle comprising:
   providing a surgical suture having a leading end and a trailing end;
   using a first suture gripper to secure the leading end of said surgical suture;
   advancing said first suture gripper downstream toward a surgical needle having a suture receiving end and inserting the leading end of said surgical suture into said suture receiving end of said surgical needle, wherein said first suture gripper applies a first tension level to said surgical suture;
   performing a swaging operation for attaching the leading end of said surgical suture to said suture receiving end of said surgical needle while maintaining the first tension level on said surgical suture;
   using a second suture gripper to secure said surgical suture at a location that is upstream from said first suture gripper;
   advancing said second suture gripper downstream toward said first suture gripper and said surgical needle for reducing the tension applied to a section of said surgical suture that extends between said second suture gripper and said surgical needle to a second tension level that is less than the first tension level;
   after the reducing the tension step, releasing said first suture gripper from the leading end of said surgical suture and moving said first suture gripper to a location that is upstream from said second suture gripper;
   after the releasing and moving said first suture gripper steps, closing said first suture gripper to secure a section of said surgical suture at a location upstream of said second suture gripper; and
   cutting said surgical suture at a location between said first and second suture grippers to form a cut suture section that extends between said surgical needle and said second suture gripper.

2. The method as claimed in claim 1, further comprising:
   securing said surgical needle using a needle gripper; and
   after the cutting step, using said needle gripper and said second suture gripper to transfer said surgical needle and said cut suture section to a pull test station.

3. The method as claimed in claim 2, further comprising moving said second suture gripper away from said needle gripper as said surgical needle and said cut suture section are transferred to said pull test station for increasing the tension in said cut suture section from the second tension level to a third tension level that is greater than the second tension level.

4. The method as claimed in claim 3, wherein the first tension level is about 50-200 grams, the second tension level is about 15-25 grams, and the third tension level is about 40 grams.

5. The method as claimed in claim 3, further comprising:
at said pull test station, using a third suture gripper to secure said cut suture section at a location between said surgical needle and said second suture gripper; and
moving said third suture gripper away from said surgical needle for increasing tension on said cut suture section to a fourth tension level that is greater than the third tension level.

6. The method as claimed in claim 1, further comprising:
providing a spool of suture;
using said first suture gripper for dispensing a length of said surgical suture from said spool of suture; and
passing said dispensed length of said surgical suture though a tension device located between said spool of suture and said first suture gripper for maintaining tension applied to said dispensed length of surgical suture at the first tension level.

7. The method as claimed in claim 1, wherein said first and third suture grippers comprise electric cylinders, and said second suture gripper device is a programmable electric actuator comprising moving coil technology or voice coil actuator technology.

8. The method as claimed in claim 1, further comprising a central processing unit for automatically controlling operation of said first, second and third suture grippers and said needle gripper, wherein said central processing unit contains different programs for manufacturing armed surgical needles having differently sized surgical needles and differently sized sutures.

9. The method as claimed in claim 1, wherein during the cutting step the tension applied to said suture between said first suture gripper and said second suture gripper is about 50-200 grams, and the tension applied to said suture between said second suture gripper and said surgical needle is about 15-25 grams.

* * * * *